US012796951B2

(12) United States Patent
Greiser et al.

(10) Patent No.: US 12,796,951 B2
(45) Date of Patent: Nov. 17, 2026

(54) MAGNETIC RESONANCE MEASUREMENT ON A SET OF TEETH

(71) Applicant: Siemens Healthineers AG, Forchheim (DE)

(72) Inventors: Andreas Greiser, Erlangen (DE); Thomas Beck, Dormitz (DE); Julian Wohlers, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 154 days.

(21) Appl. No.: 17/997,332

(22) PCT Filed: Apr. 8, 2021

(86) PCT No.: PCT/EP2021/059190

§ 371 (c)(1),
(2) Date: Oct. 27, 2022

(87) PCT Pub. No.: WO2021/219340

PCT Pub. Date: Nov. 4, 2021

(65) Prior Publication Data

US 2023/0165481 A1 Jun. 1, 2023

(30) Foreign Application Priority Data

Apr. 29, 2020 (DE) ......................... 102020205432.0

(51) Int. Cl.
*A61B 5/055* (2006.01)
*A61B 5/00* (2006.01)
(Continued)

(52) U.S. Cl.
CPC .............. *A61B 5/055* (2013.01); *A61B 5/004* (2013.01); *A61B 5/4547* (2013.01); *A61B 5/704* (2013.01);
(Continued)

(58) Field of Classification Search
CPC ... A61B 2562/182; A61B 5/004; A61B 5/055; A61B 5/4547; A61B 5/682;
(Continued)

(56) References Cited

U.S. PATENT DOCUMENTS 6,681,771 B2 * 1/2004 Durette .................. A61B 90/04 128/842
2006/0241406 A1 10/2006 Noujeim
(Continued)

FOREIGN PATENT DOCUMENTS

CN 105188527 A 12/2015
CN 109803586 A 5/2019
(Continued)

OTHER PUBLICATIONS

Noras MRI Products “Mandibula 15-Channel Dental Coil” https://www.noras.de/en/mri-products/mandibula-15-ch-dental-coil/; Date of screenshot: Oct. 25, 2022.
(Continued)

*Primary Examiner* — Michael J Carey
*Assistant Examiner* — Maria Christina Talty
(74) *Attorney, Agent, or Firm* — Banner & Witcoff, Ltd.

(57) ABSTRACT

An antenna array for receiving radio-frequency signals in a frequency and power range of a magnetic resonance apparatus. The antenna array includes: a signal conductor configured to receive a radio-frequency signal of a magnetic alternating field and to transmit the radio-frequency signal to the magnetic resonance apparatus; and a carrier element mechanically connected to the signal conductor, wherein the carrier element is shaped in accordance with at least part of a set of teeth of an examination object, and wherein the carrier element is positively connectable to the set of teeth of the examination object in an application-appropriate position in accordance with an application in order to
(Continued)

position the signal conductor on the set of teeth of the examination object.

12 Claims, 8 Drawing Sheets

(51) Int. Cl.
*G01R 33/34* (2006.01)
*G01R 33/48* (2006.01)

(52) U.S. Cl.
CPC ... *G01R 33/34084* (2013.01); *G01R 33/4818* (2013.01)

(58) Field of Classification Search
CPC ........ G01R 33/34007; G01R 33/34084; G01R 33/3415; G01R 33/4818
See application file for complete search history.

(56) References Cited

U.S. PATENT DOCUMENTS

| | | | | |
|---|---|---|---|---|
| 2011/0038514 | A1* | 2/2011 | Weigl | A61C 9/0053 382/128 |
| 2012/0041298 | A1* | 2/2012 | Mersky | A61B 6/482 324/309 |
| 2014/0084923 | A1* | 3/2014 | Grodzki | G01R 33/561 324/309 |
| 2014/0213888 | A1* | 7/2014 | Idiyatullin | A61B 5/055 324/309 |
| 2016/0022142 | A1 | 1/2016 | Bradshaw | |
| 2016/0231401 | A1* | 8/2016 | Wang | A61B 5/4547 |
| 2017/0265978 | A1* | 9/2017 | Borotto | A61C 19/05 |
| 2018/0000563 | A1* | 1/2018 | Shanjani | A61C 7/002 |
| 2021/0018579 | A1* | 1/2021 | Nixdorf | A61C 9/0046 |

FOREIGN PATENT DOCUMENTS

| | | | | |
|---|---|---|---|---|
| DE | 202007008008 | U1 | 10/2007 | |
| DE | 102012217483 | A1 | 3/2014 | |
| DE | 202015105111 | U1 * | 12/2015 | G01R 33/34061 |
| KR | 102095273 | B1 | 4/2020 | |

OTHER PUBLICATIONS

Tymofiyeva O. et al.: "In Vivo MRI-Based Dental Impression Using an Intraoral RF Receiver Coil" in Concepts Magn. Reson., 33B: 244-251. https://doi.org/10.1002/cmr.b.20126; 2008.

Ludwig U. et al.: "Dental MRI using wireless intraoral coils", Sci Rep 6, 23301 (2016), https://doi.org/10.1038/srep23301.

Bracher et al., "Feasibility of Ultra-Short Echo Time (UTE) Magnetic Resonance Imaging for Identification of Carious Lesions", Magnetic Resonance in Medicine 66, pp. 538-545 (2011); 2011.

Idiyatullin et al. "Intraoral approach for imaging teeth using the transverse B1 field components of an occlusally priented loop coil", NIH Public Access Author Manuscript, Magn Reson Med. Jul. 2014 ; 72(1): 160-165. doi:10.1002/mrm.24893.

Idiyatullin D et al.: "Dental MRI: Making the Invisible Visible", NIH Public Access Author Manuscript, J Endod Jun. 3, 20117(6): 745-752. doi: 10.1016/j.joen.2011.02.022.

Jul. 30, 2021 (PCT) International Search Report—App PCT/EP2021/059190.

* cited by examiner

MAGNETIC RESONANCE MEASUREMENT ON A SET OF TEETH

TECHNICAL FIELD

The disclosure relates to an antenna array for receiving radio-frequency signals in the frequency and power range of a magnetic resonance apparatus, comprising at least one signal conductor and a carrier element, which is connected to the antenna array, wherein the carrier element is shaped in accordance with at least part of a set of teeth of an examination object and can be positively connected in a position in accordance with the application to the set of teeth of the examination object. The disclosure relates, moreover, to a system, comprising a magnetic resonance apparatus and an antenna array, wherein the magnetic resonance apparatus has a signal link to the antenna array, and to a method for carrying out a magnetic resonance measurement of a set of teeth of an examination object with an antenna array, wherein the antenna array is connected in a predetermined relative position to the set of teeth of the examination object.

BACKGROUND

The jaw and teeth region is currently diagnosed and treated primarily on the basis of X-ray imaging methods, which potentially expose patients to ionizing radiation. This exposure of patients to radiation may be avoided by the use of imaging methods based on magnetic resonance. Such methods have hitherto been associated with technical challenges, however, which make a broad application difficult.

Firstly, the regions to be represented, such as teeth, roots of teeth or teeth defects for example, have a comparatively low volume, which is available for signal generation. Secondly, the oral cavity with the tongue, jaw and cheek regions of the patient constitutes a region of the human body with a lot of movement, and this can result in image artifacts, such as diffuse image noise or ghost images for example, during a conventional measurement duration of a magnetic resonance measurement. Primarily unconscious movements with the tongue and swallowing movements of the patient present problems here since they cannot always be arbitrarily paused over longer periods. For these reasons, the measurement duration of a magnetic resonance measurement of the oral cavity should be kept as short as possible.

To compensate the low signal volume, receive antennas have to be brought up very close locally to the anatomical region of the patient to be examined Conventional volume and surface coils, such as head coils and lay-on coils for example, are externally attached to the patient and have a relatively large spacing from the oral cavity of the patient. The achievable spacings are frequently too high to obtain high-quality images. In addition, the patient movement in the oral cavity may not be limited by external antenna systems. With a measurement duration of several minutes it should therefore be anticipated that the anatomy in the imaging region moves, for example due to swallowing movements or tensing of the jaw musculature.

To provide an economically interesting alternative to X-ray-based imaging methods, magnetic resonance apparatuses with a low field strength are also necessary, which conventionally have a low signal-to-noise ratio and thus make operation with external antenna systems difficult.

A potential solution is presented by intraoral antenna systems, which can be introduced into the oral cavity of the patient and be positioned locally at the anatomy to be examined. The low signal-to-noise ratio of magnetic resonance apparatuses with low field strengths may be partially compensated as a result. A positioning of antenna systems in the oral cavity of the patient can cause undesirable reactions of the patient, however, such as retching for example, increased saliva production and involuntary sweeping with the tongue. Without further measures these reactions result in image artifacts, in particular since the tongue is in the immediate vicinity of the imaging signal conductors of the antenna system. In addition, the oral cavity with the dental arches and the tongue provide a complex, spatial geometry, which is also characterized by soft tissue, such as the tongue muscle and the cheeks. This makes stable positioning of the signal conductors difficult, above all in the regions with a high soft tissue content. In addition, the geometries of the jawbones and of the set of teeth of different patients can diverge strongly, for which reason prototypical developments in this field are associated with an individual adjustment of the antennas to the set of teeth of a test person. This would denote high costs and a high level of complexity in a medical application, which is opposed to the broad use of magnetic resonance methods as imaging for the jaw and teeth regions.

SUMMARY

The disclosure is therefore based on an object of providing a method and an apparatus, which increases the image quality of magnetic resonance examinations of the teeth and jaw regions and can be applied to a large number of patients.

The disclosed antenna array for receiving radio-frequency signals in the frequency and power range of a magnetic resonance apparatus comprises a signal conductor, which is designed to receive a radio-frequency signal of a magnetic alternating field and to transmit it to the magnetic resonance apparatus, and a carrier element, which is connected to the signal conductor.

An antenna array for receiving radio-frequency signals can be represented by a coupling element between electromagnetic waves or magnetic alternating fields guided and unguided in conductors, in other words, located in a free space. The antenna array is preferably designed to receive electromagnetic waves in the range of the magnetic resonance frequencies of different magnetic resonance-active atomic nuclei. For example, an electromagnetic wave with a frequency between 1 and 500 MHz, preferably between 10 and 300 MHz, is regarded as a radio-frequency signal. The magnetic resonance signal of conventional atomic nuclei to be examined can have a low power of a few microwatts to several milliwatts.

A signal conductor is preferably an electrically conductive wire in which a current is induced by a magnetic alternating field. The wire of the signal conductor can have any oval or polygonal cross-section, which is suitable for transmitting the powers indicated above. It is likewise conceivable that the signal conductor is designed as a track on a printed circuit board and has an approximately rectangular cross-section. Preferably, the signal conductor is made of copper. Other electrically conductive metals, such as gold or aluminum for example, and combinations thereof, such as a silver-coated or a gold-coated signal conductor made of copper for example, are also conceivable, however. The signal conductor and/or the antenna array preferably have a contact protection feature, which protects the examination object against voltages and/or burns. The antenna array and/or the signal conductor can have, for example, a coating and/or a covering made of plastic for this purpose. Suitable plastics are, for example, polytetrafluorethylene (PTFE) or various polysiloxanes.

For transmitting the received magnetic resonance signals to the magnetic resonance apparatus, the signal conductor is preferably electrically connected to the magnetic resonance apparatus. It is conceivable that the antenna array and magnetic resonance apparatus are connected via an electrical connection cable, which electrically connects the antenna array to the magnetic resonance apparatus. An electrical connection cable of this kind can be, for example, a coaxial cable, which has a shield in order to avoid electromagnetic interspersion from the surroundings. The electrical connection cable is preferably connected to a corresponding physical interface of a receiver. It is likewise conceivable, however, that the antenna array is connected to the magnetic resonance apparatus without cables. The antenna array can have a transmitter for this purpose, which transmits measured magnetic resonance signals to the magnetic resonance apparatus by means of the emission of electromagnetic or acoustic waves. The magnetic resonance apparatus can have a corresponding receiver, which is suitable for receiving the signals of the transmitter of the antenna array.

It is also conceivable that the antenna array has an electronic circuit, which is connected to the signal conductor. The electronic circuit can comprise a union of one or more electronic component(s), such as transistors, resistors, capacitors, diodes, PCB tracks and the like for example. The electronic circuit can in particular have a protective circuit, which is suitable for protecting the antenna array against overload. For the avoidance of magnetic attraction forces, standing waves, heating and comparable, undesirable effects, the electronic circuit can have a high proportion of non-magnetic materials and corresponding standing wave barriers and/or baluns. The electronic circuit preferably has a printed circuit board (PCB) or a comparable carrier structure, which is capable of receiving the electronic components in a predetermined position relative to each other.

A carrier element preferably provides a holder for the signal conductor and/or the antenna array and is mechanically connected thereto. A mechanical connection can occur by way of any positive, non-positive and/or material-fit connection. It is conceivable, for example, that the antenna array is glued or screwed to the carrier element. The signal conductor and/or the antenna array can likewise be suspended, clamped or inserted in or welded to the carrier element, however. A structural stability of the signal conductor and/or the antenna array may be increased by way of the connection to the carrier element. For this purpose, the carrier element preferably has a dimensionally stable, electrically insulating material. It is also conceivable that the material of the carrier element is non-magnetic or has a low interaction with magnetic fields. Since in the position in accordance with the application the carrier element can be positively connected to the set of teeth of the examination object, the material of the carrier element preferably also has high biocompatibility. A material with high biocompatibility is characterized in particular by high cell and blood compatibility and is preferably histopathologically harmless. Possible materials are, for example, plastics such as silicones, polyethers, polyamides, polycarbonates but also polymers of various natural products such as proteins, saccharides, peptides and the like. In addition, ceramics, such as aluminum oxide, gypsum, hydroxyl apatite and the like for example are also conceivable. For example a mammal, preferably a primate and particularly preferably a human, is regarded as an examination object.

The carrier element of the antenna array is shaped in accordance with at least part of the set of teeth of an examination object, wherein the carrier element can be positively connected in a position in accordance with the application to the set of teeth of the examination object in order to position the signal conductor of the antenna array on the set of teeth of the examination object.

A position of the carrier element in accordance with the application preferably exists when the carrier element is positively connected to the set of teeth of the examination object. It is conceivable that a spacing between the set of teeth and carrier element is minimal in the position of the carrier element in accordance with the application, so the signal conductor of the antenna array is positioned as close as possible to the set of teeth of the examination object. The connection between carrier element and set of teeth is positive. This can mean that a shape of the carrier element and a shape of the set of teeth fit together or mesh in such a way that a freedom of movement of the carrier element in the position in accordance with the application is limited at least in one spatial direction by the set of teeth. It is likewise conceivable that at least one degree of freedom of the movement, such as a rotational movement or a translational movement for example, is limited by the set of teeth. The set of teeth can comprise part of a tooth, an interdental space, a tooth, several teeth, a dental arch or several dental arches. The set of teeth can also be toothless, in other words, part of a dental arch or an entire dental arch without teeth. A dental arch typically has a periodontium or part of the periodontium with all teeth or some of the teeth of an upper jaw or a lower jaw. Preferably, the set of teeth and the carrier element touch at least at one point in the position in accordance with the application. It is desirable, however, that in the position of the carrier element in accordance with the application, the carrier element and the set of teeth touch at a plurality of points in order to delimit the freedom of movement of the carrier element. An outer shape of the carrier element is preferably shaped such that the carrier element may be introduced into an open oral cavity of the examination object, in particular of a human.

The positioning of the antenna array in accordance with the application may be advantageously simplified by the use of a carrier element shaped in accordance with the set of teeth of the examination object. In addition, a signal-to-noise ratio and an image quality of the magnetic resonance examination may be advantageously increased by an intraoral positioning of the antenna array in the vicinity of an anatomy relevant to the imaging.

In one aspect of the disclosed antenna array, the antenna array is designed to emit radio-frequency signals into the examination object in the frequency and power range of a magnetic resonance apparatus. The antenna array can have one or more dedicated signal conductor(s) for this purpose for transmitting radio-frequency signals. It is also conceivable, however, that one or more signal conductor(s) is/are alternately used for transmitting and for receiving radio-frequency signals. For excitation of the nuclear spins in the examination object, a transmitting power of the antenna array can typically lie, as a function of the static magnetic field of the magnetic resonance apparatus, in a power range of a few watts to several kilowatts. The cross-section of the signal conductors, the contact protection feature and/or the electronic circuit of the antenna array are preferably coordinated with the transmitting power of the antenna array and can supply this permanently.

It is conceivable that the antenna array generates a magnetic alternating field B1, which briefly deflects the orientation of the atomic nuclei in the examination object from an orientation with a static magnetic field B0. It is likewise conceivable that the antenna array receives a magnetic resonance signal of the atomic nuclei deflected by the magnetic alternating field B1 and transmits it to the magnetic resonance apparatus. A signal conductor for transmitting radio-frequency signals can be arranged on the carrier element and be positioned in the position in accordance with the application on the set of teeth of the examination object. It is also conceivable, however, that a signal conductor for transmitting the radio-frequency signals is arranged outside of the oral cavity and has a signal link to the antenna array. An external arrangement of corresponding signal conductors can at least partially enclose the head of the examination object. The external arrangement preferably has a cage-like (birdcage) or drum-like structure, which generates a circular or linear polarized magnetic field in an interior.

Magnetic alternating fields can be generated in a locally dedicated manner and detected due to the use of an antenna array for transmitting and receiving radio-frequency signals. The low signal volume in the oral cavity of the examination object may advantageously be represented with a higher sensitivity as a result.

In accordance with one aspect of the disclosed antenna array, the signal conductor of the antenna array is embedded in a material of the carrier element. The signal conductor is preferably embedded along a surface of the carrier element, so the spacing from a surface of the set of teeth in the position of the carrier element in accordance with the application is as small as possible at the set of teeth. The signal conductor can be completely let into the material of the carrier element or partially protrude from the surface of the carrier element. The signal conductor is preferably enclosed by the material of the carrier element. It is conceivable that the material of the carrier element produces the contact protection feature of the signal conductor in relation to the examination object.

It is also conceivable that at least some of electronic circuit of the antenna array is embedded in the carrier element.

The contact protection feature of the antenna array may advantageously be provided by the carrier element by way of the embedding of the signal conductor in the material of the carrier element. Furthermore, the signal conductor and/or the electrical circuit of the antenna array in the carrier element can be protected against aggressive influences of conventional sterilization and cleaning methods, so the antenna array can advantageously be cleaned and reused.

In a further aspect of the antenna array, the signal conductor of the antenna array has a loop, which is shaped in accordance with at least part of a dental arch of the examination object. A loop represents, for example, an approximately loop-shaped section of the signal conductor. The loop can also have other shapes, however. For example an oval shape, a polygonal and any geometric deformation of these shapes is conceivable. It is likewise conceivable that the loop can have the shape of a lemniscate or can be obtained from said shapes by torsion, folding and/or distortion. At least part of the loop is shaped in accordance with part of a dental arch of the examination object. This can mean that the loop follows the trajectory of the dental arch at least over a section of the dental arch. Preferably, the loop follows the trajectory of the dental arch at least along half of a dental arch. It is likewise conceivable, however, that the loop follows the entire dental arch and terminates with one end of the dental arch. The end of the dental arch can be, for example, a tooth positioned terminally in the direction of the throat of the examination object. The end of the dental arch can also be an incisor, however, which constitutes the first tooth of the dental arch pointing in the direction of the oral cavity of the examination object. It is also conceivable that the signal conductor of the loop is guided once or several times over a section of the dental arch.

A loop-shaped signal conductor can typically be inexpensively produced. Owing to a simple shaping the loop may advantageously adjust to the carrier element and/or be integrated therein. Manufacturing expenditure for the antenna array can be reduced as a result.

In a further aspect of the disclosed antenna array, the antenna array has an array of signal conductors, wherein the array of signal conductors is shaped in accordance with at least part of the dental arch. An array of signal conductors preferably comprises a plurality of signal conductors, which is connected to the magnetic resonance apparatus and/or the electronic circuit. It is conceivable in particular that each signal conductor of the plurality of signal conductors is electrically connected to a receiver channel of the magnetic resonance apparatus. Furthermore, the signal conductors of the plurality of signal conductors can also be connected among themselves.

A signal conductor can have a loop in accordance with one of the above-described shapes. Preferably, the loops of the signal conductors have an oval shape. The loops can be arranged, for example, to adjoin each other or partially overlap in a matrix, which is shaped in accordance with at least part of the dental arch. Furthermore, the matrix can have a regular or a non-regular arrangement of the plurality of signal conductors. In addition, a grid-like arrangement of the plurality of signal conductors in the matrix is also conceivable.

Covering the relevant anatomy with signal conductors may advantageously be improved by the use of the array of signal conductors. As a result, the signal-to-noise ratio can be increased and the image quality of the magnetic resonance examination improved. In addition, when a plurality of receiver channels is used, parallel imaging algorithms may be employed, which reconstruct image data of the examination object from subsampled k-space data and enable a reduction of the measurement duration of the magnetic resonance measurement.

In accordance with a further aspect of the disclosed antenna array, at least some of the array of signal conductors is oriented along a plane of a biting surface of the examination object. As described above, the array of signal conductors can have a matrix of adjacent or partially overlapping loops. The array of signal conductors preferably has a shape adapted to the dental arch of the examination object, such as a U-shape or a horseshoe shape for example. It is conceivable that the array of signal conductors may be positioned along a plane of a biting surface of a dental arch between the dental arch of the upper jaw and the dental arch of the lower jaw. The array of signal conductors preferably has an approximately planar extension, which enables imaging with an approximate occlusion position of the dental arches. Preferably, at least a part of a dental arch relevant to the imaging is covered along the biting surface by the antenna array. It is likewise conceivable, however, that the array of signal conductors with the carrier element in the position in accordance with the application is selectively connected to the dental arch of the upper jaw or the lower jaw of the examination object.

A sensitivity distribution of the antenna array in the region of the tooth and/or the neck of a tooth can be improved by the positioning of the array of signal conductors along the biting surface of a dental arch. At the same time, the sensitivity distribution of the antenna array in the region of the moving cheeks and the tongue may be reduced, whereby image artifacts are advantageously suppressed. Furthermore, the improved sensitivity distribution in the region of the teeth and/or necks of the teeth in the occlusion position of the set of teeth can advantageously be used for imaging both dental arches of the examination object.

In a further aspect of the disclosed antenna array, at least part of the array of signal conductors is oriented in a perpendicular orientation to the plane of the biting surface at the inner side of the teeth of the dental arch. Starting from the plane of the biting surface, an orientation perpendicular to the plane of the biting surface can point, for example, in the direction of a hyoid bone or in the direction of a gum of the examination object. It is conceivable that the array of signal conductors in the position of the carrier element in accordance with the application is positioned on the set of teeth of the examination object on the inner side of the teeth of the examination object. Preferably, the inner side of the teeth of a dental arch is at least partially enclosed by the array of signal conductors. The array of signal conductors can also project over part of a gingiva of the examination object. It is thus conceivable that the array of signal conductors encloses the entire inner surface of the teeth of a dental arch starting from a plane of the biting surface through to the projection of the gingiva, but also part of the gingiva. Preferably, the array of signal conductors is oriented approximately parallel to the inner surface of the teeth. The dental arch can be both a dental arch of the lower jaw as well as a dental arch of the upper jaw. It is likewise conceivable that the array of signal conductors in the position of the carrier element in accordance with the application is positioned both on the inner surface of the teeth of the upper jaw as well as the inner surface of the teeth of the lower jaw.

The set of teeth of the examination object may advantageously be enclosed by signal conductors from several sides due to the positioning of the array of signal conductors on the inner surface of the teeth of the examination object. As a result, the signal-to-noise ratio of the magnetic resonance measurement can be increased and the image quality improved. Furthermore, a minimum spacing from the set of teeth with the greatest possible spacing from the moving cheeks can be produced by positioning the array of signal conductors on the inner surface of the teeth. The freedom of movement of the tongue may be limited by the positioning of the array of signal conductors on the inner surface of the teeth, moreover, whereby image artifacts due to movement of the tongue may advantageously be reduced.

In a further aspect of the disclosed antenna array, at least part of the array of signal conductors is oriented in a perpendicular orientation to the plane of the biting surface on an outer side of the teeth of the dental arch. It is conceivable that the array of signal conductors in the position of the carrier element in accordance with the application is positioned on the set of teeth of the examination object on the outer side of the teeth of the examination object. Preferably, the outer side of the teeth is at least partially enclosed by the array of signal conductors. The array of the signal conductors can also project over part of a gingiva of the examination object. Preferably, the array of signal conductors is oriented approximately parallel to the outer surface of the teeth. It is conceivable that the array of signal conductors molds around the entire outer surface of the teeth of a dental arch starting from a plane of the biting surface through to the projection of the gingiva, but also beyond. The dental arch can be both a dental arch of the lower jaw as well as a dental arch of the upper jaw. It is likewise conceivable that the array of signal conductors in the position of the carrier element in accordance with the application is positioned both on the outer surface of the teeth of the upper jaw and on the outer surface of the teeth of the lower jaw.

The set of teeth of the examination object may advantageously be enclosed by signal conductors from several sides due to the positioning of the array of signal conductors on the outer surface of the teeth of the examination object. As a result, the signal-to-noise ratio of the magnetic resonance measurement can be increased and the image quality improved. Furthermore, compared to the inner surface of the teeth, the outer surface of the teeth conventionally has a larger and/or more uniform surface, which enables an advantageous distribution of the array of signal conductors. An improved signal reconstruction may be achieved as a result when accelerated, parallel imaging methods are used, such as iPAT (integrated parallel acquisition techniques) or SMS (simultaneous multi slicing) for example.

In accordance with one aspect of the disclosed antenna array, the carrier element encloses the dental arch of the examination object in a position in accordance with the application at least along one side of the teeth at which the signal conductor or the array of signal conductors is positioned. A side of the teeth can be, for example, the inner surface of the teeth, the outer surface of the teeth or the biting surface of the dental arch or part of the dental arch. It is conceivable that the carrier element encloses the dental arch from all sides at which the signal conductor or the array of signal conductors is positioned. Preferably, the carrier element extends approximately parallel along the side of the teeth. This can mean that at least part of the carrier element is oriented parallel to the biting surface, the inner side of the teeth and/or the outer side of the teeth of the dental arch. It is likewise conceivable that the carrier element is shaped in accordance with the dental arch by way of an enclosure of the dental arch on one, two or more side(s) of the dental arch. Preferably, the signal conductor or the array of signal conductors is stabilized or supported along the side of the teeth by means of the connection to the carrier element.

In this aspect, the signal conductor or the array of signal conductors, in the position in accordance with the application, is positioned on a side of the carrier element facing the dental arch. This can mean that the signal conductor or the array of signal conductors is positioned on a side of the carrier element, which is shaped in accordance with the set of teeth of the examination object. The signal conductor or the array of signal conductors can, as described above, be connected positively, non-positively or with a material fit to the carrier element in any manner. It is likewise conceivable that the signal conductor or the array of signal conductors is inserted in the carrier element and when connected to the set of teeth is clamped between the dental arch and the carrier element.

A positive connection between the carrier element and the set of teeth of the examination object can advantageously be obtained by the enclosure of one or more side(s) of the dental arch by the carrier element. Furthermore, the signal conductor or the array of signal conductors, in the position in accordance with the application, may advantageously be dimensionally stably fixed by way of the connection to the carrier element to the set of teeth of the examination object and safeguard against a movement of the examination object during a magnetic resonance examination.

In accordance with a further aspect of the disclosed antenna array, on a side facing the dental arch in a position in accordance with the application, the carrier element has a plastic compound, which can be deformed on contact with the set of teeth of the examination object. A plastic compound is preferably plastically deformable. This can mean that the plastic compound permanently retains a shape obtained due to deformation. The plastic compound can be permanently deformable or deformable in a predetermined time window. It is conceivable, for example, that the plastic compound cures in a predetermined time due to contact with atmospheric oxygen or due to the addition of a curing component. The plastic compound can be produced for this purpose, for example in advance of the magnetic resonance examination, by way of blending. Preferably, a deformation resistance of the plastic compound is low enough to enable manual deformation and/or a deformation due to the set of teeth of the examination object at a temperature between 15° C. and 40° C. The material of the plastic compound is preferably biocompatible. In addition to the materials mentioned above, primarily plastic compounds based on gypsum, wax, hydrocolloid, silicone and polyether are conceivable. Preferably, in the position of the carrier element in accordance with the application, the plastic compound can be molded to a dental arch. This can mean that the plastic compound deforms three-dimensionally when connected to the dental arch and surrounds the dental arch from several sides. It is conceivable that the plastic compound surrounds the dental arch over a continuous section or at a plurality of disjunct points. It is likewise conceivable that the plastic compound surrounds the entire dental arch. In the position of the carrier element in accordance with the application, the plastic compound can be connected to the dental arch of the lower jaw, to the dental arch of the upper jaw or to both dental arches.

It is conceivable that in the position of the carrier element in accordance with the application, the plastic compound is applied to a surface of the carrier element facing the dental arch. A signal conductor of the antenna array can be positioned, for example, between the dental arch and the plastic compound or between the plastic compound and the carrier element. It is likewise conceivable, however, that the plastic compound is the carrier element or is part of the carrier element with which the antenna array is connected to the set of teeth of the examination object in the position in accordance with the application. In this case, a signal conductor can be positioned both between the dental arch and the plastic compound, as well as on a side of the plastic compound remote from the dental arch.

The carrier element may advantageously be positively connected to sets of teeth of any shape due to the use of a plastic compound. Expenditure for the production of individually adapted carrier elements can be reduced as a result.

In a further aspect of the disclosed antenna array, the carrier element has a recess for receiving the dental arch and a holding apparatus for fixing the signal conductor or the array of signal conductors, wherein the signal conductor or the array of signal conductors is mounted over the recess by means of the holding apparatus and by positioning the carrier element in accordance with the application on the set of teeth of the examination object, can be molded to the set of teeth of the examination object.

A recess can be, for example, an indentation, an arching or an inlet in the carrier element, which has a suitable geometry for receiving the dental arch of the examination object. A suitable geometry is in particular an indentation with a "U"-shaped, a "V"-shaped, a "C"-shaped cross-section or a cross-section with any shape, which can be obtained by distortion or deformation of said shapes. Preferably, the recess is designed to be circumferential in the carrier element, so in the position in accordance with the application at least part of the dental arch is received by the recess.

A holding apparatus can be any connecting element, which is suitable for fixing the signal conductor or the array of signal conductors. Possible examples of a holding apparatus are hanger assemblies such as hooks or eyes and glued joints, hook holes, snap-in joints and the like. Preferably, the holding apparatus has a detachable connecting element, which enables a reversible connection of the signal conductor or the array of signal conductors to the carrier element.

The signal conductor or the array of signal conductors is preferably connected to a holding apparatus at two points at least. Preferably, a holding apparatus is positioned on the carrier element in such a way that the signal conductor or the array of signal conductors is mounted over the recess of the carrier element by a connection to the holding apparatus in accordance with the application.

It is conceivable that the signal conductor or the array of signal conductors is fixed to the holding apparatus with an elastic element, such as a spring or a rubber band for example. As a result, with positioning of the carrier element on the dental arch in accordance with the application, the signal conductor or the array of signal conductors can be deflected with elongation of the elastic element by a part of the dental arch into the recess of the carrier element. The signal conductor or the array of signal conductors is preferably molded to the biting surface, the inner surface of the teeth and the outer surface of the teeth of the dental arch by means of a tensile force exerted due to stretching of the elastic element, so the signal conductor or the array of signal conductors encloses the dental arch in the recess from all sides. The signal conductor or the array of signal conductors preferably has adequate plastic and/or elastic deformability. For this purpose, the signal conductor or the array of signal conductors can comprise elements that are elastic, moveable and/or displaceable relative to each other.

In addition, the signal conductor or the array of signal conductors and/or the holding apparatus can also have a rolling or folding mechanism, which is designed to deflect the signal conductor or the array of signal conductors on contact with a dental arch. Furthermore, the holding apparatus can have any elastic systems, such as pneumatic or hydraulic spring systems for example, for fixing the signal conductor or the array of signal conductors.

When the carrier element is connected to the set of teeth of the examination object, the antenna array may advantageously mold to the dental arch due to the use of an elastic fixing of the signal conductor or the array of signal conductors. The spacing between the signal conductors or the array of signal conductors and the dental arch can advantageously be reduced as a result. An improved signal-to-noise ratio of the magnetic resonance measurement may be achieved in this way.

In a further aspect of the disclosed antenna array, in the position in accordance with the application, at least part of the antenna array is positioned along part of a gum and/or a hyoid bone of the examination object. It is conceivable that the antenna array, as described above, encloses at least part of the gingiva of the examination object. Analogously, the antenna array can enclose the inner side of the teeth from a biting surface through to the gum and/or the hyoid bone of the examination object. It is conceivable in particular that the carrier element has an arcuate structure, which is shaped in accordance with the gum and/or the hyoid bone of the examination object and in the position of the carrier element in accordance with the application, is connected to the gum and/or the hyoid bone. The arcuate structure can have a flexible material, such as a rubber- or silicon-based elastomer for example, which can be molded to the gum and/or the hyoid bone when the carrier element is connected to the set of teeth.

The arcuate structure of the carrier element can be connected to the signal conductor or the array of signal conductors and position it at least along part of the gum and/or the hyoid bone. It is conceivable that the signal conductor or the array of signal conductors can be deformed as described above and adjusts to a shape of the gum or of the hyoid bone of the examination object. Furthermore, the signal conductor or the array of signal conductors can be molded to the gum and/or the hyoid bone of the examination object by means of the tongue of the examination object. In a natural resting position, the tongue can lie against the gum and the hyoid bone of the examination object and can mold the deformable signal conductor or the deformable array of signal conductors to the gum and/or the hyoid bone. Preferably, the carrier element has, at least in the region of a tongue base and/or root, a recess in order to avoid constriction or pinching of the tongue.

The sensitive region of the antenna array may advantageously be expanded to the entire region of the oral cavity due to the positioning of the signal conductor or the array of signal conductors in the region of the gum and/or the hyoid bone of the examination object.

In accordance with a further aspect of the disclosed antenna array, the antenna array has at least one electrically conductive shield, which in a position of the antenna array in accordance with the application, is positioned between the antenna array and a soft tissue of the examination object and is designed to shield a radio-frequency signal of a magnetic alternating field from a direction of the soft tissue.

An electrically conductive shield preferably has an electrically conductive metal, such as gold, silver or aluminum for example. It is likewise conceivable that the electrically conductive shield has a basic body made from any non-magnetic material, which is coated or galvanized with an electrically conductive material. The electrically conductive shield is in particular designed to shield radio-frequency signals, which are emitted by the soft tissue in the direction of the antenna array.

A soft tissue can be, for example, the tongue, the cheek or a lip of the examination object. Preferably, radio-frequency signals of the soft tissue are derived from the electrically conductive shield in order to reduce an interaction of such signals with the antenna array. The electrically conductive shield is positioned between the antenna array and the soft tissue for this purpose. This can mean, for example, that the electrically conductive shield is positioned in a gap between the outer side of the teeth of dental arch and the cheek of the examination object. It is likewise conceivable that the electrically conductive shield is positioned between the inner side of the teeth and the tongue of the examination object.

The electrically conductive shield can be connected in one piece to the carrier element of the antenna array or be fixed to the carrier element. Furthermore, the electrically conductive shield can have an electrical connection to the ground of the antenna array and/or the magnetic resonance apparatus. It is likewise conceivable that in a position in accordance with the application, the electrically conductive shield is separate from the antenna array and/or other electrically conductive components.

Radio-frequency signals from moving regions of the oral cavity, such as the cheeks or the tongue of the examination object for example, may advantageously be shielded due to the use of an electrically conductive shield. As a result, image artifacts may be avoided and the quality of the image data increased.

The disclosed system comprises a magnetic resonance apparatus and an antenna array, wherein the magnetic resonance apparatus has a signal link to the antenna array and is designed to receive radio-frequency signals of the antenna array and to produce image data of a set of teeth of the examination object. Preferably, the signal link between the antenna array and the magnetic resonance apparatus is configured as a shielded electrical connection cable. The electrical connection cable can moreover have further components, such as an electronic circuit, a receiver and/or an amplifier for example. It is likewise conceivable that the signal link between antenna array and magnetic resonance apparatus is configured to be wireless. For this purpose, the antenna array, as described above, can have a transmitter, which communicates with a corresponding receiver of the magnetic resonance apparatus. The communication can take place over directed or undirected, electromagnetic waves. Possible transmission methods can comprise, for example, a transmission via radio or optical directional radio. It is also conceivable that the antenna array is localized, identified and/or initialized by means of the wireless signal link. A corresponding signal link can be implemented, by way of example, by an RFID system.

Preferably, the magnetic resonance apparatus has a holder with which the antenna array and/or a carrier element is held on the set of teeth of the examination object in the position in accordance with the application. The holder can also be connected to a carrier element in accordance with one of the above-described aspects. Preferably, the holder has an adjusting mechanism with which an orientation of the antenna array and/or of the carrier element may be changed in at least two spatial directions.

It is also conceivable that a magnetic flux density and/or an orientation of the magnetic main field B0 are coordinated with the antenna array. This can mean in particular that in the position in accordance with the application, the antenna array and/or the signal conductor or the array of signal conductors are oriented approximately orthogonally to the orientation of the magnetic main field B0.

Image data of the magnetic resonance measurement can be obtained by means of repeated Fourier transform of the measurement data (k-space data) of the examination object. For an acquisition of k-space data, an orientation of atomic nuclei in the examination object in the x-, y- and z-directions are modulated with respect to the static magnetic field B0 and the radio-frequency signals of the atomic nuclei are detected by means of the at least one signal conductor. The atomic nuclei of individual slices of the examination object may be allocated specific RF pulses by way of the modulation in the z-direction, which pulses can be used for a slice selection. The modulations in the x-direction and the y-direction can imprint an additional frequency gradient and a phase gradient on the atomic nuclei, so the receiving radio-frequency signals may be assigned to a volume element in the examination object. Typically, a sum signal of the horizontal spatial frequencies is then entered in a horizontal row of a matrix, while a sum signal of the vertical spatial frequencies is entered in a vertical column of the matrix. This matrix is typically referred to as the k-space and constitutes the measurement data of the magnetic resonance measurement.

An improved signal transmission and an improved mechanical and/or electrical integration of the antenna array with the magnetic resonance apparatus may be achieved by a combination of the magnetic resonance apparatus and the antenna array in an disclosed system. When a dedicated holder is used for the antenna array and/or the carrier element, a positioning of the antenna coil in an imaging region of the magnetic resonance apparatus optimized to a geometric requirement of the magnetic resonance apparatus may advantageously be provided.

In a further aspect of the disclosed system, the magnetic resonance apparatus comprises a plurality of receiver channels, which have a plurality of signal links to an array of signal conductors. A plurality of receiver channels can mean, for example, that the receiver of the magnetic resonance apparatus has a plurality of physical interfaces, which are electrically connected to the antenna array or to an array of signal conductors of the antenna array. It is conceivable that exactly one signal conductor of the array of signal conductors is connected to exactly one receiver channel of the receiver of the magnetic resonance apparatus. It is likewise conceivable, however, that a plurality of signal conductors is connected to one receiver channel.

The signal-to-noise ratio of the magnetic resonance measurement may advantageously be improved by the use of a plurality of receiver channels for receiving magnetic resonance signals of the array of signal conductors. In addition, methods for a reconstruction of image data from reduced k-space data can be used, which advantageously reduces the necessary measurement duration for acquiring the image data.

In the disclosed method for carrying out a magnetic resonance measurement of a set of teeth of an examination object with an antenna array, the antenna array is connected to the set of teeth of the examination object in a predetermined relative position.

In one step of the disclosed method, the carrier element with the antenna array is oriented relative to the set of teeth in the oral cavity of the examination object, with a side of the carrier element shaped in accordance with the set of teeth of the examination object being oriented in a direction facing the set of teeth. As described above, the carrier element has at least one side, which is shaped in accordance with the shape of a dental arch of the examination object. An orientation of the side of the carrier element shaped in accordance with the set of teeth in a direction facing the set of teeth can be taken to mean that the carrier element is brought at least approximately into an orientation, which matches the position in accordance with the application on the set of teeth of the examination object. The orientation can deviate in any spatial direction from the position in accordance with the application in order to facilitate introduction of the carrier element into the oral cavity and/or a positioning of the carrier element in the oral cavity of the examination object. It is conceivable, for example, that the carrier element is turned or tilted with respect to the position in accordance with the application in order to facilitate introduction into the oral cavity.

The carrier element may be connected to the set of teeth only in a predetermined orientation due to the use of a carrier element shaped in accordance with the set of teeth. The positioning of the carrier element in accordance with the application may be determined on the basis of an outer form of the carrier element, whereby incorrect positioning of the antenna array is advantageously avoided.

In a further step of the disclosed method, the carrier element is connected to the set of teeth of the examination object in a position in accordance with the application. The connection occurs by bringing the side of the carrier element shaped in accordance with the set of teeth of the examination object into contact with the set of teeth.

It is conceivable that the carrier element is plastically deformed when it is connected to the set of teeth in order to obtain a positive connection to the set of teeth. It is also conceivable, however, that part of the deformation of the carrier element is an elastic deformation. Elastic restoring forces of the carrier element can act on a surface of the set of teeth and non-positively connect the carrier element to the set of teeth due to an elastic deformation of the carrier element. Preferably, as described above, the carrier element has a recess for receiving a dental arch. In a position of the carrier element in accordance with the application, the recess can mesh with the dental arch in order to limit a relative movement between the carrier element and the dental arch along a plane of the biting surface. It is also conceivable, however, that a cross-section of the recess is smaller than a corresponding cross-section of the dental arch, so the carrier element is deformed when connected to the set of teeth. As described above, a positive connection, which fixes the carrier element to the set of teeth, can be obtained due to the deformation of the carrier element. The deformation can also have elastic portions, which enable a non-positive connection to the set of teeth. The at least one signal conductor of the antenna array can be positioned on a side of the carrier element facing the set of teeth in the position in accordance with the application of the carrier element. The at least one signal conductor can be positioned with the smallest possible spacing from the set of teeth of the examination object as a result. Instead of the at least one signal conductor, the antenna array can also have an array of signal conductors in accordance with one of the above-described aspects. Preferably, when the carrier element is connected to the set of teeth, as described above, the signal conductor or the array of signal conductors are positioned in the position in accordance with the application along a biting surface, an inner side of the teeth and/or an outer side of the teeth.

Laborious positioning of the antenna array on the set of teeth of the examination object can advantageously be avoided by bringing the side of the carrier element shaped in accordance with the set of teeth into contact with the set of teeth of the examination object. A duration of the preparation of the magnetic resonance measurement may be reduced and the comfort of the examination object increased as a result.

In a further step of the disclosed method, the magnetic resonance measurement of the set of teeth of the examination object is carried out, wherein the antenna array detects radio-frequency signals by means of the at least one signal conductor and transmits them to a receiver of the magnetic resonance apparatus. The implementation of the magnetic resonance measurement preferably comprises an execution of imaging sequences, which are adapted to imaging of teeth. Possible imaging sequences can have, for example, very short echo times in order to compensate a short T2 relaxation time of spins of dentin or tooth enamel and to represent this region in the image data in a signal intense manner Very short echo times can be, for example, less than 150 μs or less than 70 μs. Possible imaging sequences are, for example, FLASH (fast low-angle shot) or UTE (ultra-short echo time) sequences. It is likewise conceivable, however, that imaging sequences with a longer echo time, such as a TSE (turbo spin echo) sequence for example, are used. With sequences of this kind, detection of the magnetic resonance signal of the tooth enamel or of the dentin can be avoided. In image data of imaging sequences of this kind, the teeth may be differentiated, for example, by the absence of a signal intensity in contrast to surrounding tissue. In the case of both imaging sequences with short as well as with longer echo times, the antenna array is positioned preferably in the immediate vicinity of a medically relevant anatomy by means of the carrier element in order to detect the magnetic resonance signals of the low signal volume of the oral cavity of the examination object. The antenna array can have both an single signal conductor as well as an array of signal conductors. Preferably, when the carrier element is connected to the set of teeth of the examination object, the signal conductor or the array of signal conductors are positioned such that a high coverage of the signal volume of the relevant anatomy is achieved.

When carrying out the magnetic resonance measurement, even low signals may advantageously be detected with the antenna array and be used for an image reconstruction due to the positioning of the antenna array in the immediate vicinity of the relevant anatomy of the examination object.

In one aspect of the disclosed method, the plastic compound of the carrier element is deformed when connected to the set of teeth and forms a positive connection with the set of teeth of the examination object, which reversibly fixes the carrier element to the set of teeth. As described above, in the position in accordance with the application, in the side facing the dental arch, the carrier element can have a plastic compound, which molds to the dental arch of the examination object. The plastic compound is preferably applied in a recess of the carrier element, which is designed to enclose the dental arch of the examination object from at least one side. As a result, the plastic compound may be supported by the carrier element at least at the one side, so the plastic compound can be molded over at least one side of the dental arch.

It is also conceivable that the plastic compound is the carrier element. The signal conductor or the array of signal conductors can in this case be positioned, in the position in accordance with the application, on a side facing the dental arch or side of the plastic compound remote from the dental arch. The signal conductor or the array of signal conductors can also be embedded in the plastic compound. In a position in accordance with the application, the plastic compound can enclose the entire dental arch or enclose it at certain points, in other words, be connected to the dental arch at individual, disjunct points. The plastic compound is preferably shaped in accordance with a shape of a dental arch. This can mean that the plastic compound has, for example, a U-shaped or a horseshoe-shaped form even before connection to the set of teeth of the examination object.

Preferably, the plastic compound is reversibly connected to the set of teeth of the examination object and may be detached from the set of teeth manually or using a suitable apparatus after a typical duration of a magnetic resonance examination, such as 5 minutes, 10 minutes, 15 minutes or 30 minutes for example. It is conceivable that the plastic compound comprises one of the above-described materials.

The carrier element may be molded to an individual geometry of the set of teeth of the examination object due to the use of a plastic compound. A laborious adjustment of the carrier element to different sizes of sets of teeth may advantageously be avoided as a result. Furthermore, due to molding of the plastic compound to the set of teeth of the examination object, a positive connection to the set of teeth can be obtained, which advantageously avoids a relative movement between the antenna array and the set of teeth of the examination object, for example due to an involuntary movement of the tongue, the cheeks or of the jaw of the examination object.

In one aspect, the disclosed method has a further step in which the carrier element is detached from the set of teeth of the examination object and a positive mold of the set of teeth of the examination object is produced on the basis of the plastic compound of the carrier element. A positive mold can represent a realistic model of the set of teeth of an examination object, which can be used, for example, as a dental impression for the production of a dental prosthesis. It is conceivable that the positive mold of the set of teeth is obtained from a negative mold of the plastic compound of the carrier element. For this purpose, the plastic compound, which after molding to the set of teeth of the examination object has an impression of the set of teeth of the examination object, can be removed from the set of teeth of the examination object and be filled with any molding compound.

The magnetic resonance measurement may advantageously be combined with the production of a dental impression due to the use of the plastic compound for the connection of the carrier element to the set of teeth of the examination object. The workflow of a dental facility may advantageously be optimized and treatment costs reduced due to the simultaneous production of image data of the examination object and the dental impression.

In a further aspect of the disclosed method, the signal conductor or the array of signal conductors is mounted over the recess of the carrier element by means of the holding apparatus and when the carrier element is connected to the set of teeth, is deflected by at least part of the dental arch in a direction of the carrier element facing the recess, with at least part of the dental arch being enclosed along a free surface by the signal conductor or the array of signal conductors.

In this aspect, as described above, the signal conductor or the array of signal conductors can have elements which are deformable or can move against each other, which allow molding to the dental arch of the examination object. Preferably, the holding apparatus also has an elastically deformable element on which the signal conductor or the array of signal conductors is mounted or suspended. It is conceivable that with a deflection in the direction of the recess, the signal conductor or the array of signal conductors is stretched over a free surface of the dental arch, so the signal conductor or the array of signal conductors encloses the dental arch. A free surface of the dental arch can be, for example, a contour of a tooth, which follows the surface of the tooth along the inner side of the teeth, the biting surface and the outer side of the teeth.

Preferably, as described above, the signal conductor or the array of signal conductors, has a coating and/or a covering made from an electrically and/or thermally insulating material in order to avoid damage to a tooth or injury to the examination object.

It is conceivable that the signal conductor or the array of signal conductors is permanently pressed into the recess of the carrier element by means of a bite force of the examination object. Preferably, a restoring force of a jaw muscle of the examination object is utilized, however, in order to keep the signal conductor or the array of signal conductors in the recess of the carrier element. For this purpose, the two dental arches of the examination object can be spaced so far apart from each other by the carrier element that a natural restoring force of the jaw musculature pulls the two dental arches onto each other and presses the signal conductor or the array of signal conductors into the recess of the carrier element. A spacing between the two dental arches can be achieved, for example, by means of an arbitrarily shaped spacer, which is positioned between the two dental arches. The spacer is preferably connected in one piece to the carrier element. A design of the spacer separate from the carrier element is also conceivable, however.

The antenna array may advantageously be adapted to any geometry of the dental arch due to the stretching of the signal conductor or the array of signal conductors on the dental arch of the examination object. Complex adjustments of the carrier element to a large number of possible shapes of sets of teeth can be avoided as a result.

In a further aspect of the disclosed method, the magnetic resonance measurement is carried out with a plurality of receiver channels, which receives magnetic resonance signals from the array of signal conductors, with a reduced volume of k-space data being acquired and parallel imaging methods being used to reduce a measurement duration of the magnetic resonance measurement, in order to reconstruct image data of the set of teeth from the reduced volume of k-space data.

It is conceivable that the plurality of receiver channels simultaneously detects a plurality of magnetic resonance signals of the array of signal conductors. Preferably, individual signal conductors of the array of signal conductors have different spatial sensitivities, which can be used as additional coding for the reconstruction of the image data. Acquisition of a reduced volume of k-space data is preferably achieved by a reduction in the number of phase-encoded steps in the imaging sequence. With a constant image resolution this can result in a reduction of the imaging region. An anatomy with greater dimensions than the reduced imaging region can cause convolution artifacts, which may be removed by the application of reconstruction methods of parallel imaging. It is conceivable that reconstruction methods are used, which reconstruct the data of the k-space. Possible reconstruction methods are, for example, SMASH (simultaneous acquisition of spatial harmonics), GRAPPA (generalized auto-calibrating partially parallel acquisitions), PILS (parallel imaging with localized sensitivities) and SENSE (sensitivity encoding). It is likewise conceivable, however, that the reconstruction method comprises a Fourier transform of k-space data. Furthermore, SMS (simultaneous multi slice) imaging methods can also be used to accelerate the acquisition of the k-space data.

An acquired volume of k-space data may be reduced and the image data reconstructed by means of the parallel imaging methods due to receiving a plurality of magnetic resonance signals of the array of signal conductors by means of a plurality of receiver channels. The measurement duration of the magnetic resonance measurement may advantageously be reduced as a result. This can increase the comfort of the examination object and increase the cost-effectiveness and the penetration capacity of imaging methods based on magnetic resonance with respect to existing systems based on ionizing radiation.

DESCRIPTION OF THE DRAWINGS

Further advantages and details can be found in the following description of exemplary aspects in connection with the drawings. In the drawings, in a schematic diagram.

DETAILED DESCRIPTION

Reference will be made in the following description of the figures to a human patient as the examination object since this represents a customary application for imaging methods based on magnetic resonance. This of course does not preclude an application to the above-described examples of examination objects.

Figure 1:
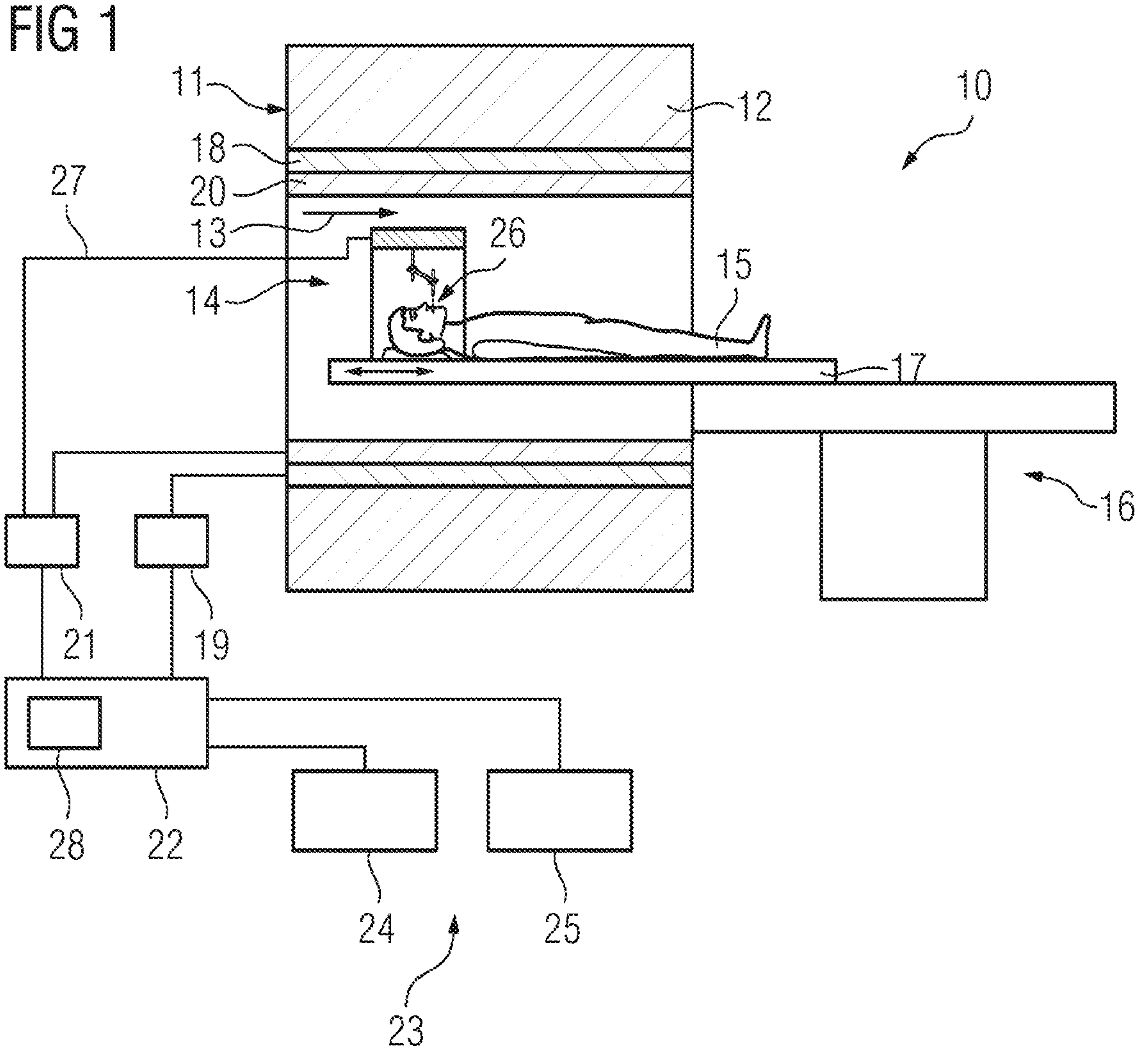
FIG. 1 shows one possible aspect of an disclosed system.

FIG. 1 schematically represents an aspect of the system with a magnetic resonance apparatus 10 and an antenna array 26. The magnetic resonance apparatus 10 comprises a magnetic unit 11, which has, for example, a permanent magnet, an electromagnet or a superconductive main magnet 12 for generating a strong starken and, in particular, homogeneous main magnetic field 13 (static magnetic field B0). In addition, the magnetic resonance apparatus 10 comprises a patient-receiving region 14 for receiving a patient. In the present exemplary aspect, the patient-receiving region 14 is cylindrical and surrounded in a circumferential direction by the magnetic unit 11. Basically, designs of the patient-receiving region 14 that differ from this example are also conceivable, however.

The patient can be positioned in the patient-receiving region 14 by means of a patient-positioning apparatus 16 of the magnetic resonance apparatus 10. The patient-positioning apparatus 16 has for this purpose a patient couch 17 configured to move inner side the patient-receiving region 14. The magnetic unit 11 also has a gradient coil 18 for generating magnetic field gradients, which is used for spatial encoding during imaging. The gradient coil 18 is actuated by means of a gradient control unit 19 of the magnetic resonance apparatus 10. The magnetic unit 11 can also comprise a radio-frequency antenna, which in the present exemplary aspect is designed as a body coil 20 permanently integrated in the magnetic resonance apparatus 10. The body coil 20 is configured for exciting atomic nuclei, which are located in the main magnetic field 13 generated by the main magnet 12. The body coil 20 is actuated by a radio-frequency unit 21 of the magnetic resonance apparatus 10 and irradiates radio-frequency signals into an examination space, which is substantially formed by a patient-receiving region 14 of the magnetic resonance apparatus 10. The body coil 20 is also designed for receiving magnetic resonance signals.

The magnetic resonance apparatus 10 has a control unit 22 for controlling the main magnet 12, the gradient control unit 19 and for controlling the radio-frequency unit 21. The control unit 22 is designed to carry out a sequence, such as an imaging gradient echo sequence, a TSE sequence or a UTE sequence for example. In addition, the control unit 22 comprises an evaluation unit 28 for evaluating digitized magnetic resonance signals, which are detected during the magnetic resonance examination. The evaluation unit can likewise be designed to use reconstruction methods in order to reconstruct image data from reduced volumes of k-space data when parallel imaging methods are used.

Furthermore, the magnetic resonance apparatus 10 comprises a user interface 23, which has a signal link to the control unit 22. Control information, such as imaging parameters and reconstructed magnetic resonance images, can be displayed for a user on a display unit 24, for example on at least one monitor, of the user interface 23. Furthermore, the user interface 23 has an input unit 25 by means of which parameters of a magnetic resonance measurement can be input by the user. Furthermore, the magnetic resonance apparatus 10 has an antenna array 26, which is positioned on the set of teeth of an examination object 15 and transmits magnetic resonance signals from the oral cavity to the magnetic resonance apparatus 10. The antenna array 26 preferably has an electrical connection cable 27, which provides a signal link to the radio-frequency unit 21 and the control unit 22. Just like the body coil 20, the antenna array 26 can also be designed for exciting atomic nuclei and for receiving magnetic resonance signals. The antenna array 26 can have, in particular, a drum-shaped construction for this purpose, which surrounds the head of the patient 15. The antenna array 26 is actuated by the radio-frequency unit 21 for emitting radio-frequency signals.

The represented magnetic resonance apparatus 10 can of course comprise further components, which magnetic resonance apparatuses conventionally have. It is likewise conceivable that instead of the cylindrical construction, the magnetic resonance apparatus 10 has a C-shaped, a triangular or an asymmetric construction of the magnetic field-generating components. The magnetic resonance apparatus 10 can be designed in particular to carry out a magnetic resonance examination of a standing or seated patient 15.

Figure 2:
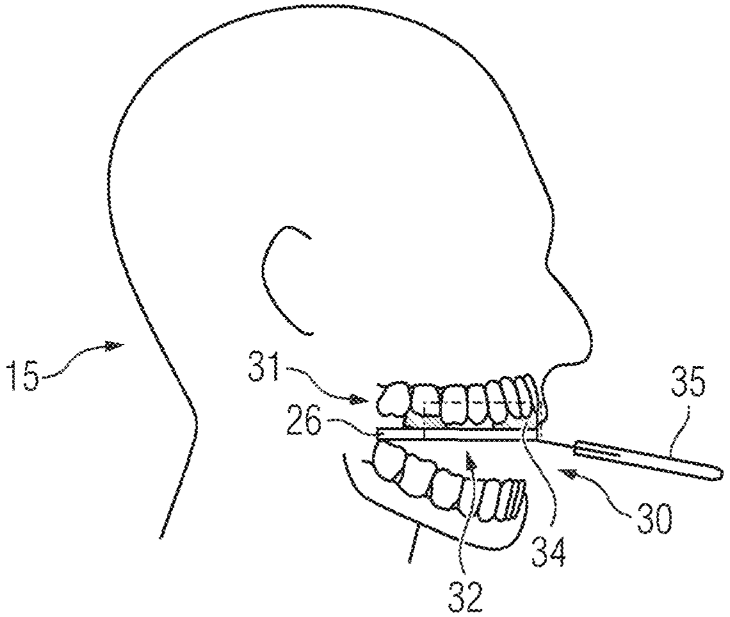
FIG. 2 shows one possible aspect of an disclosed antenna array with a plastic compound.

FIG. 2 shows an aspect of the antenna array 26 in which the antenna array 26 is connected to the dental arch 31 of the upper jaw of the patient 15 by means of the plastic compound 34. In the example shown, a suitably shaped applicator 35 is used to connect the antenna array 26 to the plastic compound 34, in the position in accordance with the application, to the dental arch 31 of the patient 15. The plastic compound 34 represents the carrier element, which positively connects the antenna array 26 to the set of teeth 30 of the patient. The plastic compound 34 is applied to a plurality of disjunct points of the antenna array 26 for this purpose. In this aspect, the antenna array 26 has a horseshoe shape, which is shaped in accordance with the shape of the dental arch 31. The antenna array 26 is encased with an electrically and thermally insulating material in order to protect the patient 15.

Figure 3:
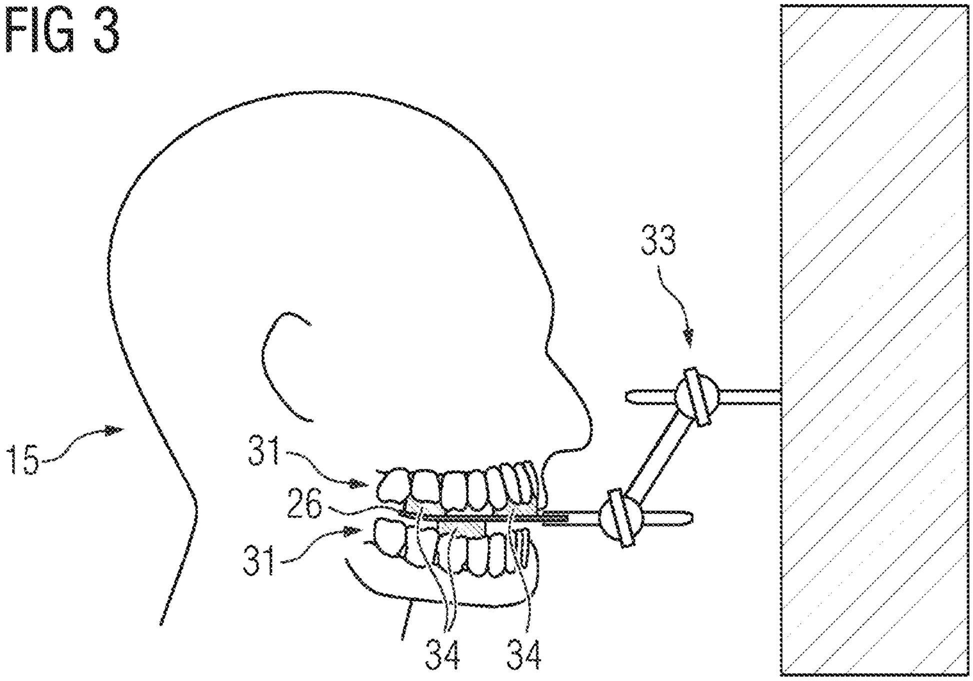
FIG. 3 shows one possible aspect of an disclosed antenna array with a plastic compound.

FIG. 3 shows an alternative aspect of the antenna array 26 in which the antenna array 26 is connected to the dental arches 31 of the upper and lower jaws of the patient 15 by means of the plastic compound 34. In this example, the antenna array 26 is fixed to a holder 33, which has an adjusting mechanism for adjusting the orientation of the antenna array 26 in all three spatial directions. Both the applicator 35 and the holder 33 can be suitable for leading a signal conductor of the antenna array 26 out of the oral cavity 32 of the patient 15 and/or providing a connection to an electrical connection cable 27. For example, a strain relief for the electrical connection cable 27 and/or the signal conductor of the antenna array 26 can be provided for this purpose.

Figure 4:
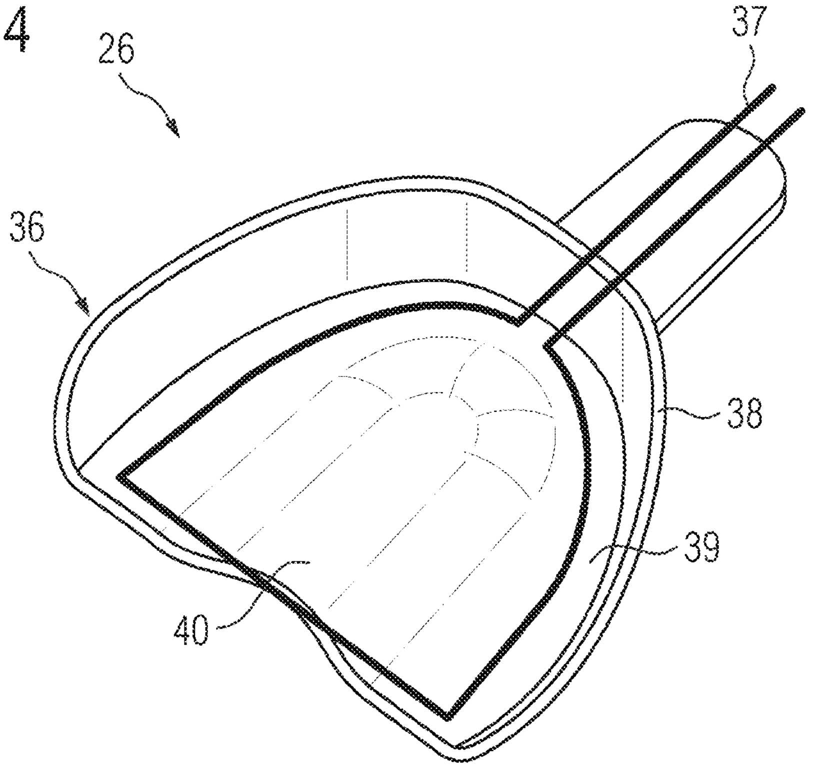
FIG. 4 shows one possible aspect of an disclosed antenna array.

FIG. 4 shows an aspect of the antenna array 26, which has a non-plastic carrier element 36. The carrier element 36 is shaped in accordance with the dental arch 31 of the patient 15 and has an encircling wall 38, which, in the position in accordance with the application, is positioned on the outer side of the teeth of the dental arch 31 and limits the movement of the carrier element 36 along the plane of the biting surface. The carrier element 36 also has a recess 39, which, in the position in accordance with the application, receives the dental arch 31 of the patient. In a position in accordance with the application, an arcuate structure 40 of the carrier element 36 rests on the gum of the patient 15 and limits the movement of the carrier element 36 in the direction of the inner side of the teeth of the dental arch 31. In the example shown, the carrier element 36 is shaped in accordance with the dental arch 31 of a patient 15 and thus enables a positive connection of the antenna array 26 with the set of teeth 30 of the patient 15. It is conceivable that the recess 39 also has a plastic compound 34, which improves the positive connection between the dental arch 31 and the antenna array 26. In the example shown, the antenna array 26 has an individual loop of a signal conductor 37, which runs along the recess 39 and in the position in accordance with the application, is positioned on a biting surface of the dental arch 31.

Figure 5:
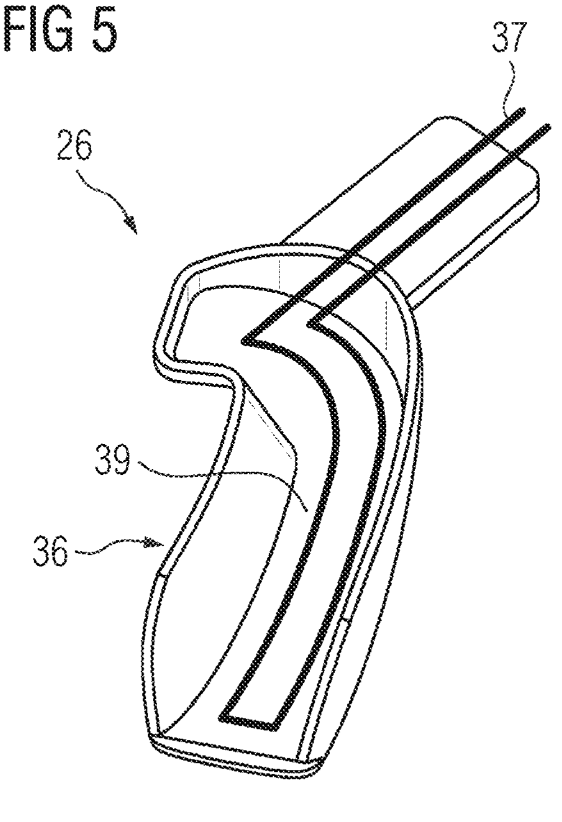
FIG. 5 shows one possible aspect of an disclosed antenna array.

FIG. 5 shows an alternative aspect of the antenna array 26 in which the carrier element 36 encloses part of the dental arch 31. In the illustrated example, the carrier element 36 encloses a quadrant of the dental arch 31, which typically comprises two incisors, a canine and premolars and molars. In addition to the illustrated example, further configurations of the carrier element 36 are also conceivable, which enclose individual sections or one or more quadrant(s) of the dental arch 31. As in the aspect shown in FIG. 4, the loop of the signal conductor 37 is inserted in the recess 39. At the side of the carrier element 36 facing the pharynx of the patient 15 in accordance with the application direction, the loop has a deflection of 180°, so the signal conductor 37 is inserted in the recess 39 with a double wire. This can improve the sensitivity of the antenna array 26 in the region of the enclosed dental arch 31. It is also conceivable, however, that a section of the signal conductor 37 is led back outside of the recess 39 or the carrier element 36 in order to close the loop.

Figure 6:
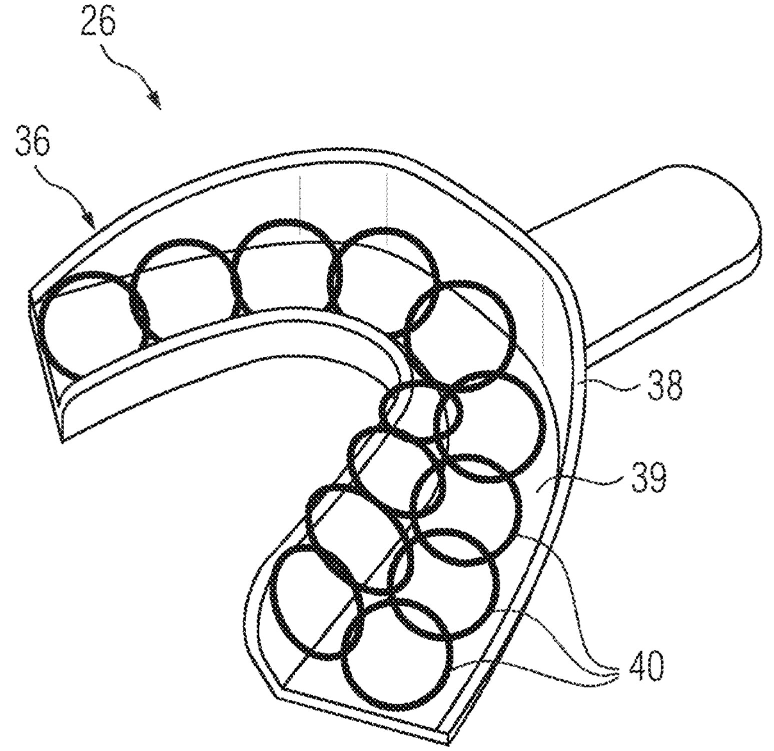
FIG. 6 shows one possible aspect of an disclosed antenna array with an array of signal conductors.

FIG. 6 shows an aspect of the antenna array 26 in which an array of signal conductors 40 is positioned in the recess 39 of the carrier element 36. In the illustrated example, the array of signal conductors 40 has an array or a matrix of adjoining, partially overlapping, circular rings. The array of signal conductors 40 can also have a grid structure and any linear or non-linear arrangements of the signal conductors 37, however. In the illustrated aspect, part of the array of signal conductors 40 is positioned on the walls 38 of the carrier element 36 adjoining the inner side of the teeth of the dental arch 31 in the position in accordance with the application. The sensitivity of the array of signal conductors 40 along the inner side of the teeth of the dental arch 31 is increased hereby. It is conceivable that the wall 38 of the carrier element 36 positioned on the outer side of the teeth also has an array of signal conductors 40, so the dental arch 31 of the patient 15 is enclosed by signal conductors 37 along the inner side of the teeth, the biting surface and the outer side of the teeth.

Figure 7:
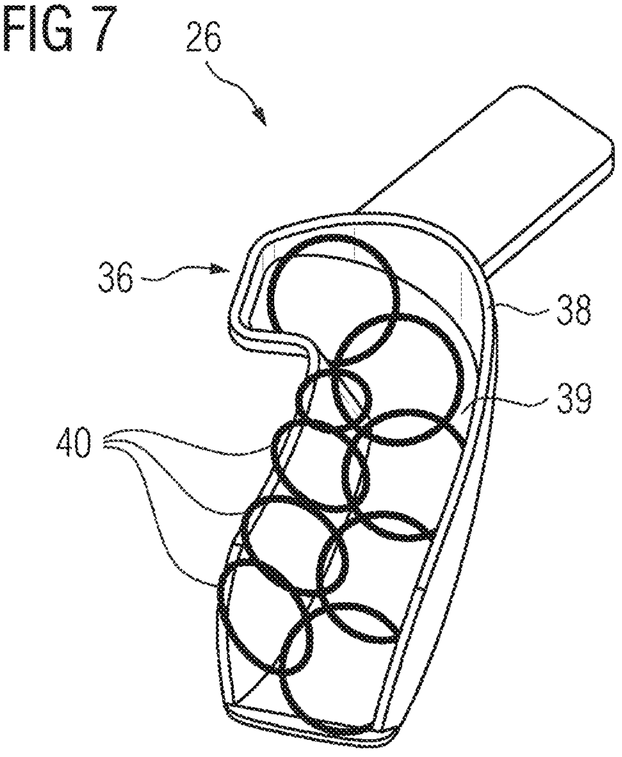
FIG. 7 shows one possible aspect of an disclosed antenna array with an array of signal conductors.

FIG. 7 shows an alternative aspect of the antenna array 26 represented in FIG. 6 in which the antenna array 26 encloses a quadrant of the dental arch 31 of the patient 15. Analogously to the aspect in FIG. 6, the array of signal conductors 40 is inserted in the recess 39 of the carrier element 36 and in a position of the carrier element 36 in accordance with the application, is positioned on the biting surface and at the inner side of the teeth of the dental arch 31 of the patient 15.

The exemplary aspects shown in FIGS. 4 to 7 can in each case be shaped in accordance with the dental arch 31 of the upper or lower jaw of the patient 15. It is conceivable that two separate antenna arrays 26 are connected to the two dental arches of the patient 15 in order to enclose the entire set of teeth of the patient 15. Alternatively, the antenna array 26 has a one-piece carrier element 36, which on an upper side and a lower side has recesses 39 for receiving the dental arches of the patient 15.

Figure 8:
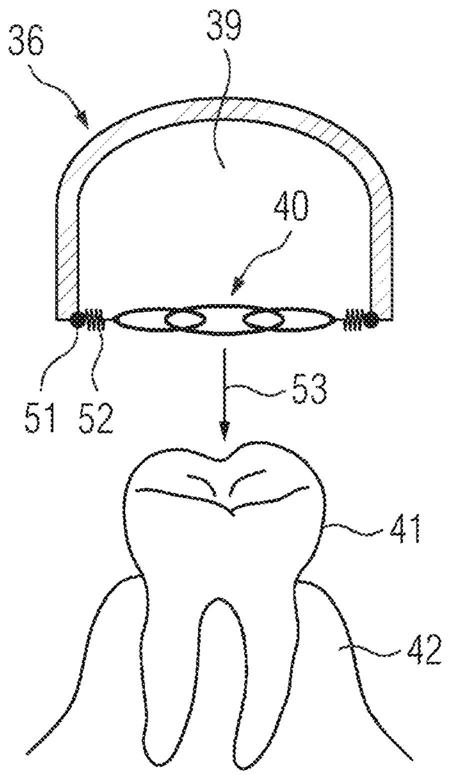
FIG. 8 shows one possible aspect of an disclosed antenna array with a holding apparatus.

FIG. 8 shows a schematic cross-section through part of the carrier element 36 of an antenna array 26 with a holding apparatus 51. The cross-section shows the recess 39 of the carrier element 36, which receives the tooth 41 of the patient 15. The carrier element 36 of the antenna array 26 is guided along a connecting direction 53 on the tooth 41 for this purpose, with the array of signal conductors 40 being deflected in the direction of the recess 39 and molded over the tooth 41. The array of signal conductors 40 is mounted by means of the elastic element 52 of the holding apparatus 51. In the illustrated example, the elastic element 52 is a spring, which stretches the array of signal conductors 40 over the tooth 41 in the position in accordance with the application. Instead of a signal conductor 37, the antenna array 26 can also have a single signal conductor 37. In this aspect, the signal conductor 37 or the array of signal conductors 40 is at least so deformable or flexible such that it can be adapted to the surface contour of the tooth 41 without damage. As indicated in FIG. 8, the array of signal conductors 40 can have elements which are flexible and/or displaceable against each other for this purpose.

Figure 9:
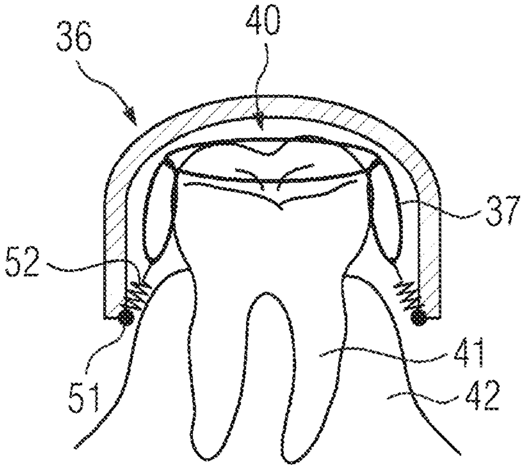
FIG. 9 shows one possible aspect of an disclosed antenna array with a holding apparatus.

FIG. 9 shows the aspect in FIG. 8, with the carrier element 36, in the position in accordance with the application, being positioned on the dental arch 31 of the patient 15. The elastic element 52 is elastically deflected with respect to the illustration in FIG. 8 and stretches the array of signal conductors 40 over the tooth 41. The tooth 41 is enclosed along its free surface by the array of signal conductors 40. The array of signal conductors 40 is positioned on the inner side of the teeth, the biting surface and the outer side of the tooth 41 as a result. In the aspect shown, part of the carrier element 36 projects over the gingiva 42 of the patient 15. The array of signal conductors 40 preferably has a coating and/or covering (not shown), which provides thermal and electrical insulation of the signal conductor 37 from the tooth 41.

Figure 10:
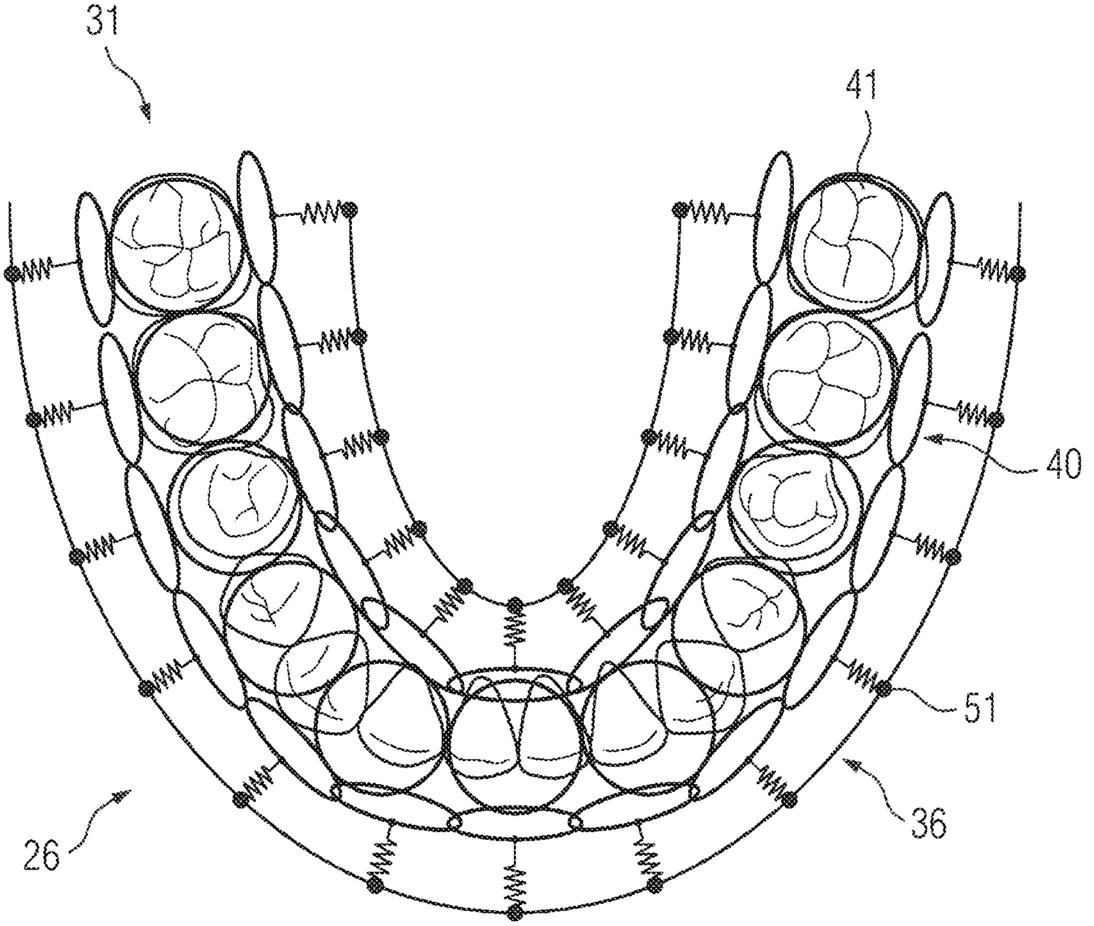
FIG. 10 shows one possible aspect of an disclosed antenna array with a holding apparatus.

FIG. 10 shows an aspect of the antenna array 26 with a holding apparatus 51 in the position in accordance with the application on the dental arch 31 of the lower jaw of the patient 15. In the illustrated aspect, a plurality of arrays of signal conductors 37 is in each case connected to the carrier element 36 on both sides of the dental arch 31 by holding facilities 51. The plurality of arrays of signal conductors 37 can be positioned side by side or partially overlap. It is conceivable that an array of signal conductors 40 is provided for each tooth 41. An array of signal conductors 40 can also, however, enclose any part of the dental arch 31, such as a plurality of teeth for example.

Figure 11:
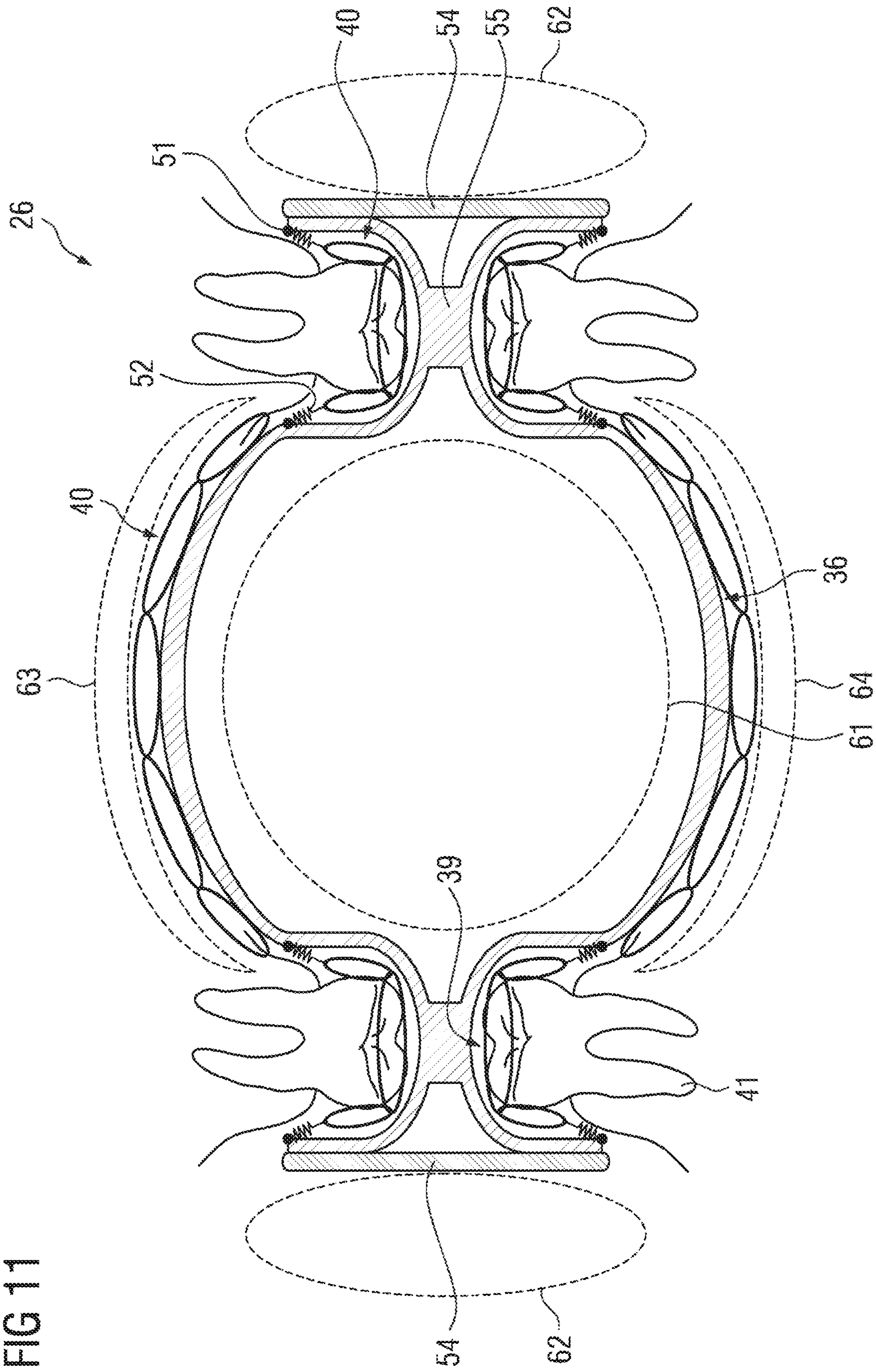
FIG. 11 shows one possible aspect of an disclosed antenna array with a holding apparatus.

FIG. 11 shows an aspect of the antenna array 26 with an electrically conductive shield 54. In this example, the carrier element 36 is designed in one piece and has in each case an encircling recess 39 for receiving the dental arches 31 of the upper and lower jaw. The electrically conductive shield 54 is positioned between the cheek 62 and the outer side of the teeth of the patient 15 and shields radio-frequency signals coming from the direction of the cheeks 62 from the antenna array 26. In the illustrated example, two electrically conductive shields 54 are positioned on both cheeks of the patient 15. It is conceivable that the antenna array 26 also has an electrically conductive shield 54 between the inner side of the teeth and the tongue 61 of the patient 15. This can be connected, for example, to the carrier element 36 or be separate from it. Preferably, for shielding magnetic resonance signals of the tongue 61, the electrically conductive shield 54 is designed to be encircling at the inner side of the teeth of the dental arch 31. In the illustrated aspect, the carrier element 36 also has a spacer 55, which produces a predetermined spacing between the two dental arches 31 in the position of the carrier element 36 in accordance with the application. The spacing is measured such that the jaw musculature of the patient 15 is stretched and a restoring force exerted on the carrier element 36, which presses the dental arches 31 against the elastic tensile force of the elastic element 52 into the recesses 39 of the carrier element 36.

The illustrated aspect also has arrays of signal conductors 37, which are positioned in an arcuate manner on the gum 63 and hyoid bone 64 of the patient 15. The arrays of signal conductors 37 are connected here to the arcuate structures on the gum and hyoid bone of the carrier element 36. It is conceivable that the side of the carrier element 36 facing the tongue 61 likewise has electrically conductive shields 54 along the gum 63 and the hyoid bone 64 in order to shield radio-frequency signals of the moving tongue 61 from the arrays of signal conductors 37 on the gum 63 and hyoid bone 64.

Figure 12:
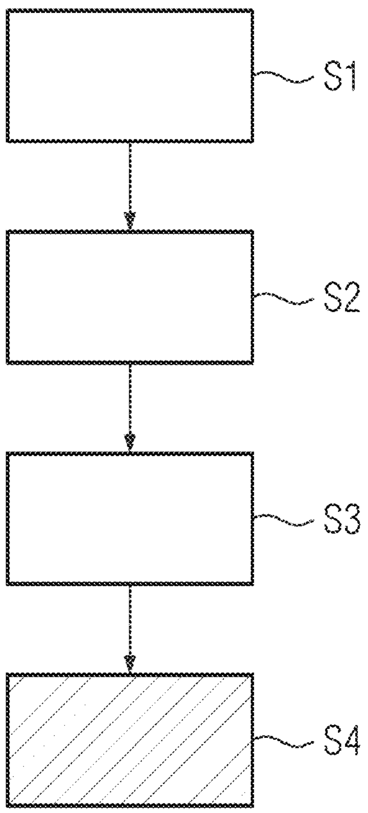
FIG. 12 shows one possible flowchart of an disclosed method.

FIG. 12 shows one possible flowchart of the disclosed method for carrying out a magnetic resonance measurement of the set of teeth of a patient 15. The steps for positioning the antenna array 26 in the position in accordance with the application on the set of teeth 30 of the patient 15 can take place, for example automatically or in a remote-controlled manner, with an appropriate apparatus.

In a step S1 of the disclosed method, the carrier element 36 with the antenna array 26 is oriented relative to the set of teeth 30 of the patient 15, with a side of the carrier element 36 shaped in accordance with the set of teeth 30 being oriented with the set of teeth 30 of the patient 15 in a direction facing the set of teeth 30. The carrier element 36 is oriented outside of the oral cavity of the patient 15. The orientation of the carrier element 36 may be determined on the basis of the shape of the carrier element 36, which is shaped in accordance with the set of teeth 30 of the patient 15. For example, a plane defined by the recess 39 is oriented with the plane of the biting surface of a dental arch 31 of the patient 15 or has a small angle with respect to this plane. The antenna array can be oriented for example with the aid of a camera in that image data of one or more camera(s) is used for calculating the orientation of the carrier element 36 relative to the set of teeth 30 of the patient 15.

In a further step S2 of the disclosed method, the carrier element 36 is connected to the set of teeth 30 of the patient 15 in a position in accordance with the application in that the carrier element 36 is brought in contact with the set of teeth 30 with the side shaped in accordance with the set of teeth 30. In the position in accordance with the application, the carrier element 36 forms a positive connection with the set of teeth 30, so a movement of the antenna array 26 relative to the set of teeth 30 of the patient 15 is avoided during the magnetic resonance examination. A freedom of movement of the tongue and/or a jaw of the patient 15 is limited by the positioning of the carrier element 36 in the position in accordance with the application in order to reduce image artifacts due to movements of the patient 15.

In one aspect of the disclosed method, in a recess 39 facing the dental arch 31 of the patient 15, the carrier element 36 has a plastic compound 34, which molds to the dental arch 31 of the patient 15 when the carrier element 36 is connected to the set of teeth 30. The plastic compound 34 forms a positive connection to the dental arch 31 and fixes the antenna array 26 reversibly to the set of teeth 30 of the patient 15. The distribution of the plastic compound 34 on the dental arch 31 can be assisted by an encircling wall 38 on the inner side of the teeth and/or outer side of the teeth, which presses the plastic compound onto the free surface of the teeth 41, so even interdental spaces are filled with the plastic compound 34.

In accordance with a further aspect of the disclosed method, the array of signal conductors 40 of the antenna array 26 is mounted over the recess 39 of the carrier element 36 by means of the holding apparatus 51 and deflected by at least part of the dental arch 31 in a direction of the carrier element 36 facing the recess 39 when the carrier element 36 is connected to the set of teeth 30. The dental arch 31 is guided in the connecting direction 53 into the recess 39 of the carrier element 36 in order to produce a position of the antenna array 26 in accordance with the application on the set of teeth 30 of the patient 15. The array of signal conductors 40 is stretched over the free surface of the dental arch 31 on deflection due to the dental arch 31 of the patient 15 by way of the elastic element 52 of the holding apparatus 51, so the inner side of the teeth, the biting surface and the outer side of the teeth of the dental arch is enclosed by the array of signal conductors 40.

In a step S3 of the disclosed method, the magnetic resonance measurement of the set of teeth 30 of the patient 15 is carried out, with the antenna array 26 detecting radio-frequency signals by means of the at least one signal conductor 37 and transmitting them to a receiver of the magnetic resonance apparatus. As described above, the radio-frequency signals can be transmitted in a wired manner or wirelessly. In the case of the wired design, the antenna array is connected to the radio-frequency unit 21 by the electrical connection cable 27, which unit represents the receiver of the magnetic resonance apparatus.

For carrying out the magnetic resonance measurement, imaging sequences are used, which allow a good differentiation of the set of teeth 30 from the surrounding tissue. As described above, imaging sequences with a very short echo time or relatively long echo time can be used here, which represent the dentin and the tooth enamel of the patient 15 in the image data in a signal intense or signal-free manner.

In one possible aspect of the disclosed method, the radio-frequency signals of the array of signal conductors 40 are detected with a plurality of receiver channels, and this enables the use of parallel imaging methods. A reduction in the measurement duration of the magnetic resonance measurement is achieved by acquiring a reduced volume of k-space data, in particular by reducing the number of phase-encoding steps. The k-space data is subsequently reconstructed by the evaluation unit 28 of the magnetic resonance apparatus 10 using reconstruction methods in order to generate the image data of the set of teeth 30 of the patient 15.

In an optional step S4 of the disclosed method, the carrier element 36 with the plastic compound 34 is detached from the set of teeth of the patient 15 and used to produce a positive mold of the set of teeth 30. For this purpose, the plastic compound 34 with the impression of the set of teeth 30 of the patient 15 is filled, as described above, with a molding compound. After curing of the molding compound the carrier element 36 is detached from the molding compound to obtain the positive mold of the set of teeth 30 of the patient 15. The positive mold can be used, for example, as a model for producing a dental prosthesis of the patient 15. It is likewise conceivable, however, that the positive mold is used for dedicated production of an adapted antenna array 26 for further magnetic resonance examinations.

Of course the order of the above-described method steps is not fixed. Individual steps, such as the production of a positive mold of the set of teeth 30 of the patient 15 for example, can also be carried out in an order different to that described here.

Although the disclosure has been illustrated and described in detail by the preferred exemplary aspects, the disclosure is nevertheless not limited by the disclosed examples and a person skilled in the art can derive other variations herefrom without departing from the scope of the disclosure.

The invention claimed is:

1. An antenna array for receiving radio-frequency signals in a frequency and power range of a magnetic resonance apparatus, the antenna array comprising:

a signal conductor configured to receive a radio-frequency signal of a magnetic alternating field and to transmit the radio-frequency signal to the magnetic resonance apparatus, wherein the signal conductor comprises a loop shaped in accordance with at least part of a dental arch of an examination object;

a carrier element mechanically connected to the signal conductor, wherein the carrier element is shaped in accordance with at least part of a set of teeth of the examination object, and wherein the carrier element is positively connectable to the set of teeth of the examination object in an application-appropriate position in accordance with an application in order to position the signal conductor on the set of teeth of the examination object; and an array of signal conductors shaped in accordance with at least part of the dental arch, wherein at least part of the array of signal conductors is orientable in a perpendicular orientation to a plane of a biting surface on an inner side of teeth of the dental arch or an outside of teeth of the dental arch, and wherein the array of signal conductors is positioned such that the signal conductor or the array of signal conductors encloses the dental arch of the examination object along a free surface of the teeth from the inner side through the biting surface to an outer side of the teeth.

2. The antenna array as claimed in claim 1, wherein the antenna array is configured to emit radio-frequency signals into the examination object in the frequency and power range of the magnetic resonance apparatus.

3. The antenna array as claimed in claim 1, wherein the signal conductor is embedded in a material of the carrier element.

4. The antenna array as claimed in claim 1, wherein at least part of the array of signal conductors is orientable along a plane of a biting surface of the examination object.

5. The antenna array as claimed in claim 1, wherein at least part of the antenna array is configured to be positioned in a position in accordance with the application along part of a gum and/or a hyoid bone of the examination object.

6. The antenna array as claimed in claim 1, wherein the antenna array has at least one electrically conductive shield which is positionable in a position of the antenna array in accordance with the application between the antenna array and a soft tissue of the examination object, and is designed to shield the radio-frequency signal of the magnetic alternating field from a direction of the soft tissue.

7. An antenna array for receiving radio-frequency signals in a frequency and power range of a magnetic resonance apparatus, the antenna array comprising:
- a signal conductor configured to receive a radio-frequency signal of a magnetic alternating field and to transmit the radio-frequency signal to the magnetic resonance apparatus, wherein the signal conductor comprises a loop shaped in accordance with at least part of a dental arch of an examination object;
- a carrier element mechanically connected to the signal conductor, wherein the carrier element is shaped in accordance with at least part of a set of teeth of the examination object, and
- wherein the carrier element is positively connectable to the set of teeth of the examination object in an application-appropriate position in accordance with an application in order to position the signal conductor on the set of teeth of the examination object; and
- an array of signal conductors shaped in accordance with at least part of the dental arch,
- wherein the carrier element encloses the dental arch of the examination object at least along a side of teeth on which the signal conductor or the array of signal conductors is positioned, and the signal conductor or the array of signal conductors is positionable on a side of the carrier element facing the dental arch, and
- wherein, on the side facing the dental arch, the carrier element has a plastic compound which is flexible on contact with the set of teeth of the examination object, without requiring external heating, and upon contact with the set of teeth, forms a positive connection with the set of teeth of the examination object, which reversibly fixes the carrier element to the set of teeth.

8. The antenna array as claimed in claim 7,
- wherein the carrier element has a recess configured to receive the dental arch and a holding apparatus configured to fix the signal conductor or the array of signal conductors, and
- wherein the signal conductor or the array of signal conductors is mounted over the recess by means of the holding apparatus, and by way of positioning of the carrier element in accordance with the application on the set of teeth of the examination object, is moldable to the set of teeth of the examination object.

9. A system comprising the magnetic resonance apparatus and the antenna array as claimed in claim 1, wherein the magnetic resonance apparatus has a signal link to the antenna array and is configured to receive radio-frequency signals of the antenna array and to produce image data of the set of teeth of the examination object.

10. The system as claimed in claim 9, wherein the magnetic resonance apparatus comprises a plurality of receiver channels having a plurality of signal links to the array of signal conductors.

11. A method for carrying out a magnetic resonance measurement of a set of teeth of an examination object using an antenna array for receiving radio-frequency signals in a frequency and power range of a magnetic resonance apparatus, the antenna array has a signal conductor configured to receive a radio-frequency signal of a magnetic alternating field and to transmit the radio-frequency signal to the magnetic resonance apparatus, and a carrier element mechanically connected to the signal conductor, wherein the carrier element is shaped in accordance with at least part of the set of teeth of the examination object, and the antenna array is connectable in a predetermined relative position to the set of teeth of the examination object, the method comprising:
- orienting the carrier element with the antenna array relative to the set of teeth in an oral cavity of the examination object, wherein a side of the carrier element shaped in accordance with the set of teeth is oriented with the set of teeth of the examination object in a direction facing the set of teeth;
- connecting the carrier element to the set of teeth of the examination object in a position in accordance with an application by bringing the side of the carrier element shaped in accordance with the set of teeth of the examination object into contact with the set of teeth; and
- carrying out the magnetic resonance measurement of the set of teeth of the examination object, wherein the antenna array detects radio-frequency signals using the signal conductor and transmits the radio-frequency signals to a receiver of the magnetic resonance apparatus, wherein on a side facing a dental arch in the position in accordance with the application, the carrier element has a plastic compound, which is flexible on contact with the set of teeth of the examination object, without requiring external heating, and upon contact with the set of teeth, forms a positive connection with the set of teeth of the examination object, which reversibly fixes the carrier element to the set of teeth.

12. The method as claimed in claim 11, further comprising:
- detaching the carrier element from the set of teeth of the examination object and producing a positive mold of the set of teeth of the examination object on the basis of the plastic compound of the carrier element.

* * * * *